(12) United States Patent
Lucas et al.

(10) Patent No.: US 6,828,090 B2
(45) Date of Patent: Dec. 7, 2004

(54) COMPOSITIONS, METHODS AND APPARATUSES FOR PRESERVING PLATELETS

(75) Inventors: David O. Lucas, Lafayette, CA (US); Vladimir Serebrennikov, Krasnoyarsk (RU)

(73) Assignee: Human BioSystems, Palo Alto, CA (US)

( * ) Notice: Subject to any disclaimer, the term of this patent is extended or adjusted under 35 U.S.C. 154(b) by 0 days.

(21) Appl. No.: 09/267,891

(22) Filed: Mar. 11, 1999

(65) Prior Publication Data

US 2002/0009705 A1 Jan. 24, 2002

Related U.S. Application Data

(63) Continuation-in-part of application No. 09/183,581, filed on Oct. 30, 1998.

(51) Int. Cl.[7] .......................... A01N 1/02; A61K 35/14
(52) U.S. Cl. ........................................ 435/2; 424/532
(58) Field of Search .................... 424/520, 529, 424/532; 435/2, 1.3; 436/8, 18; 514/774

(56) References Cited

U.S. PATENT DOCUMENTS

| | | | | |
|---|---|---|---|---|
| 2,662,520 A | | 12/1953 | McMahon ...................... 128/1 |
| 2,786,014 A | * | 3/1957 | Tullis ......................... 424/532 |
| 3,579,999 A | | 5/1971 | Schwartz ....................... 62/56 |
| 3,753,357 A | | 8/1973 | Schwartz ....................... 62/64 |
| 3,841,515 A | | 10/1974 | Schwartz ....................... 220/3 |
| 4,059,967 A | * | 11/1977 | Rowe et al. .................... 62/64 |
| 4,473,552 A | | 9/1984 | Jost ............................ 424/101 |
| 4,559,298 A | * | 12/1985 | Fahy ........................... 435/1.2 |
| 4,695,460 A | | 9/1987 | Holme ......................... 424/101 |
| 5,474,891 A | * | 12/1995 | Murphy ......................... 435/2 |
| 5,622,867 A | * | 4/1997 | Livesay et al. ................ 436/18 |
| 5,635,344 A | | 6/1997 | Garcia et al. ................. 435/1.1 |
| 5,827,741 A | * | 10/1998 | Beattie et al. ............... 435/374 |

FOREIGN PATENT DOCUMENTS

| | | |
|---|---|---|
| DE | 395432 | 1/1924 |
| EP | 0 232 672 | 8/1997 |
| FR | 2 600 671 | 12/1987 |
| GB | 1527655 | 10/1978 |
| SU | 1124974 | * 11/1984 |
| WO | WO 87/05468 | 9/1987 |
| WO | WO 88/01871 | 3/1988 |
| WO | WO 97/30350 | 8/1997 |

* cited by examiner

Primary Examiner—Robert A. Wax
(74) Attorney, Agent, or Firm—Wilson Sonsini Goodrich & Rosati

(57) ABSTRACT

A platelet composition suitable for direct transfusion into a patient is provided. The platelet composition includes a preservation medium comprising plasma and a gel-forming material in a concentration relative to the plasma such that the medium is in a sufficiently fluent state at about 37° C. to allow platelets to move within the medium and is in a sufficiently gelatinous state at about 5° C. to substantially prevent platelets from moving freely within the medium; and platelets.

17 Claims, 8 Drawing Sheets

US 6,828,090 B2

COMPOSITIONS, METHODS AND APPARATUSES FOR PRESERVING PLATELETS

RELATIONSHIP TO COPENDING APPLICATION

This application is a continuation-in-part of U.S. application Ser. No. 09/183,581, filed Oct. 30, 1998 entitled "METHOD AND APPARATUS FOR PRESERVING BIOLOGICAL MATERIALS", which is incorporated herein by reference.

FIELD OF THE INVENTION

The present invention relates to compositions, methods and apparatuses for preserving biological materials. More particularly, the invention relates to compositions, methods and apparatuses for the extended storage of platelets.

BACKGROUND OF THE INVENTION

Over the last 40 years the need for the therapeutic use of biological materials, such as blood, skin and other tissues, kidneys, hearts, livers and other body organs has increased dramatically. Blood and plasmas components, including red cells, platelets, clotting factors, albumin, and antibodies are isolated and used to treat various bleeding problems. In particular, platelets, essential components of the human blood, are used extensively for assisting in the control of bleeding and replacing functionally defective platelets in patients. For example, platelet transfusions are required by trauma patients who have lost significant amount of blood, patients undergoing chemotherapy that reduces the number of platelets and causes functional defects in remaining platelets, and patients with certain platelet-depleting diseases.

Constituents in whole blood include leukocytes (white blood cells), erythrocytes (red blood cells), thrombocytes, platelets and plasma. Platelets are not entire cells but small detached cell fragments or "minicells" derived from the cortical cytoplasm of large cells called megakaryocytes in the bone marrow. Platelets comprise an outer membrane and cytoplasm from the megakaryocytes which contain granules, dense bodies, dense tubular system and mitochondria. Platelets adhere specifically to the endothelial cell lining of damaged blood vessels, where they trigger and participate in hemostasis, or clotting, and release inflammatory mediators in response to contact with the endothelial cell lining. Important mediators released by platelets include serotonin and coagulation factors. Vascular breaches are repaired by platelets through adhesion and the response to damage is amplified by platelet secretions resulting in platelet aggregation and fibrin formation, i.e. stabilized clot.

It is very important to preserve platelets after their isolation from the body under conditions not only maintaining the biological activity of platelets but also suitable for clinical use. The average survival time for a platelet in the body after it leaves the bone marrow is 8–10 days. The average expected survival time for circulating platelets is 4–5 days, an average of the entire population. The average survival time for platelets after isolation from the body is about 5 days at room temperature.

The current standard and approved method for platelet storage is in a platelet bag at room temperature and limited to five days. The storage time is presumably limited by a decrease in pH due to increased lactate associated with anaerobic metabolic activity. Furthermore, the bag of platelets in plasma must be constantly in motion on a rocker to prevent aggregation. One of the disadvantages associated with preserving platelets under room temperature is the growth of bacteria in the platelet suspension. Platelets in a suspension stored in a refrigerator, albeit with suppressed bacteria growth, tend to activate upon contacting each other and aggregate.

Several approaches such as cryopreservation (freezing) techniques have yielded an increased number of platelets following storage. However, there is a limitation in the functional capacity and persistence of platelets in circulation that are recovered from such preservation conditions by using these methods. Freezing temperatures require the use of cryoprotectors such as DMSO (dimethyl sulfoxide) (Valeri, Feingold, and Marchionni, Blood, vol. 43, No. 1 (January)1974) and THROMBOSO™ to prevent damage to these biological materials. However, these cryoprotectors are cytotoxic, and typically leave a significant portion of the platelets with either reduced or no functional ability. Moreover, cryoprotectors usually require time-consuming preparation, such as rinsing processes, before the materials can be used, and cryoprotector residues often still remain afterwards. Freezing processes can store erythrocytes for more than 30 days, and leukocytes up to 12 hours only.

Other attempts to preserve platelets have included adding platelets activation inhibitors (Bode, Holme, Heaton and Swanson, Vox Sang, 60: 105–112 (1991); U.S. Pat. No. 5,622,867) or gelatin into the preservation medium (U.S. Pat. No. 2,786,014).

A need continues to exist for a storage system that will store biological materials, particularly platelets, for an extended period of time and still maintains their viability and bioactivity.

SUMMARY OF THE INVENTION

The present invention relates to compositions, methods and apparatuses for the extended storage of biological material and, in particular, platelets.

According to one embodiment, a platelet composition suitable for direct transfusion into a patient is provided comprising: a preservation medium comprising plasma and a gel-forming material in a concentration relative to the plasma such that the medium is in a sufficiently fluent state at a first temperature to allow platelets to move within the medium and is in a sufficiently gelatinous state at a second, lower temperature to substantially prevent platelets from moving freely within the medium; and platelets.

According to this embodiment, the first temperature is preferably about 37° C. and the second temperature is preferably about 5° C.

According to another embodiment, a platelet composition suitable for direct transfusion into a patient is provided comprising: a preservation medium comprising plasma and a gel-forming material in a concentration relative to the plasma such that the medium is in a sufficiently fluent state at a first temperature to allow platelets to move within the medium and is in a sufficiently gelatinous state at a second, lower temperature to substantially prevent platelets from moving freely within the medium; and platelets which have been stored within the preservation medium in a gelatinous state for at least 3 days where at least 50% of the platelets are intact and functional after the at least 3 days.

According to this embodiment, the first temperature is preferably about 37° C. and the second temperature is preferably about 5° C.

Also according to this embodiment, the platelets may be stored within the preservation medium for at least 5 days, more preferably at least 7 days. Also according to this embodiment, the platelets may be stored within the preservation medium for between 3 and 20 days, more preferably between 5 and 20 days. Longer storage of platelets is also possible.

Also according to this embodiment, the platelets may be stored within the preservation medium at a temperature less than 10° C. and preferably between −10° C. and 10° C. In one variation, the platelets are stored at a temperature between 0° C. and 10° C. at 1 ATM, more preferably at a temperature between 0° C. and 5° C. at 1 ATM. In another variation, the platelets are stored within the preservation medium at a temperature between −10° C. and 0° C. at a pressure greater than 10 ATM, more preferably at a temperature between −8° C. and −2° C. at a pressure greater than 10 ATM.

According to another embodiment, a platelet composition suitable for direct transfusion into a patient is provided comprising: a preservation medium comprising plasma and a gel-forming material in a concentration relative to the plasma such that the medium is in a sufficiently fluent state at a first temperature to allow platelets to move within the medium and is in a sufficiently gelatinous state at a second, lower temperature to substantially prevent platelets from moving freely within the medium; and platelets which have been stored within the preservation medium in a gelatinous state for at least 1 day at a pressure of at least 10 ATM and a temperature below 0° C. where at least 50% of the platelets are intact and functional after the at least 1 day.

According to this embodiment, the first temperature is preferably about 37° C. and the second temperature is preferably about 5° C.

Also according to this embodiment, the platelets may be stored within the preservation medium at a pressure of at least 30 ATM, more preferably at least 70 ATM, most preferably at least 200 ATM.

According to this embodiment, the platelets may be stored within the preservation medium for at least 3 days, more preferably at least 5 days and most preferably at least 7 days. Also according to this embodiment, the platelets may be stored within the preservation medium for between 2 and 20 days, more preferably between 3 and 20 days. Longer storage of platelets is also possible.

The present invention also relates to a variety of methods for storing platelets for direct transfusion into a patient. In one embodiment, the method comprises:

forming a fluent platelet composition comprising platelets and a preservation medium including plasma and a gel-forming material in a concentration relative to the plasma such that the medium is in a sufficiently fluent state at a first temperature to allow platelets to move within the medium and is in a sufficiently gelatinous state at a second, lower temperature to substantially prevent platelets from moving freely within the medium;

cooling the fluent preservation medium to form a sufficiently gelatinous state to substantially prevent free movement of the platelets within the preservation medium; and storing the platelets within the preservation medium in a gelatinous state for at least 3 days where at least 50% of the platelets are intact and functional after the at least 3 days.

According to this embodiment, the first temperature is preferably about 37° C. and the second temperature is preferably about 5° C.

According to this embodiment, the platelets may be stored within the preservation medium for at least 5 days, more preferably at least 7 days. Also according to this embodiment, the platelets may be stored within the preservation medium for between 3 and 20 days, more preferably between 5 and 20 days. Longer storage of platelets is also possible.

Also according to this embodiment, the platelets may be stored within the preservation medium at a temperature less than 10° C. and preferably between −10° C. and 10° C. In one variation, the platelets are stored at a temperature between 0° C. and 10° C. at 1 ATM, more preferably at a temperature between 0° C. and 5° C. at 1 ATM. In another variation, the platelets are stored within the preservation medium at a temperature between −10° C. and 0° C. at a pressure greater than 10 ATM, more preferably at a temperature between −8° C. and −2° C. at a pressure greater than 10 ATM.

According to another embodiment, a method is provided for storing platelets for direct transfusion into a patient comprising:

forming a fluent platelet composition comprising platelets and a preservation medium including plasma and a gel-forming material in a concentration relative to the plasma such that the medium is in a sufficiently fluent state at a first temperature to allow platelets to move within the medium and is in a sufficiently gelatinous state at a second, lower temperature to substantially prevent platelets from moving freely within the medium;

cooling the fluent preservation medium to form a sufficiently gelatinous state to substantially prevent free movement of the platelets within the preservation medium; and storing the platelets within the preservation medium in a gelatinous state for at least 1 day at a temperature below 0° C. and at a pressure of at least 10 ATM where at least 50% of the platelets are intact and functional after the at least 1 day.

According to this embodiment, the first temperature is about 37° C. and the second temperature is about 5° C.

According to this embodiment, the platelets are preferably stored within the preservation medium at a pressure of at least 30 ATM, more preferably at a pressure of at least 70 ATM, most preferably at a pressure of at least 200 ATM.

According to this embodiment, the platelets may be stored within the preservation medium for at least 3 days, more preferably at least 5 days, most preferably at least 7 days. Also according to this embodiment, the platelets may be stored within the preservation medium for between 3 and 20 days, more preferably between 5 and 20 days. Longer storage of platelets is also possible.

In regard to all of the above compositions and methods, it preferred that at least 65% of the platelets are intact and functional after storage, more preferably at least 75% of the platelets, most preferably at least 85% of the platelets.

Also in regard to all of the above compositions and methods, the gel-forming material preferably constitutes between 0.2% and 4% of the preservation medium although the concentration may vary depending on the particular gel-forming material used. Examples of gel-forming material that may be used include, but are not limited to gelatin, agarose, agar, pectin, carob cassia and natural or synthetic water soluble gum such as xanthan gum, konjac gum, guar gum, gum arabic, sodium alginate, carrageenan, irgacanth gum and hydroxyethyl methacrylaic.

Also in regard to all of the above compositions and methods, the preservation medium may further include an energy source. The energy source preferably constitutes between 0 and 5% of the preservation medium, more preferably between 0.25 and 5% of the preservation medium, and most preferably between 0.5 and 5% of the preservation medium. A wide variety of energy sources may be used. Most typically, the energy source is a carbohydrate, such as a sugar. Particular examples of energy sources include glucose, sucrose, mannose, fructose and galactose.

Also in regard to all of the above compositions and methods, the preservation medium may further include water soluble salts. The salt preferably constitutes between 0 and 2% of the preservation medium. Examples of salts include, but are not limited to sodium chloride, potassium chloride, magnesium chloride, sodium phosphate, potassium phosphate and sodium gluconate.

Also in regard to all of the above compositions and methods, the preservation medium may further include an anticoagulant. Examples of anticoagulants that may be used include heparin, citrate dextrose, citrate phosphate dextrose, amantadine, ajoene and ticlopidine.

Also in regard to all of the above compositions and methods, the preservation medium may further include amino acids. Examples of amino acids that may be used include arginine, lysine, aspartate and glutamate.

The present invention also relates to an apparatus for preserving biological materials. In one embodiment, the apparatus includes a chamber having a mouth and a lip, the lip having an inside surface and a top surface, the inside surface and the top surface of the lip meeting at a first radius, the top surface of the lip having a channel. The apparatus also includes a cover configured to mate with and seal the chamber, the cover having a bottom surface, the bottom surface having a protrusion and a sealing structure, the bottom surface of the cover and the protrusion meeting at a second radius, the protrusion being inserted into the mouth of the chamber when the cover is mated with the chamber, the protrusion having a side surface, the side surface of the protrusion and the inside surface of the lip defining a first gap and being substantially parallel when the cover is mated with the chamber, the bottom surface of the cover and the top surface of the lip defining a second gap and being substantially parallel when the cover is mated with the chamber, the second gap having a length greater than a width of the first gap, the sealing structure being inserted into the channel of the lip when the cover is mated with the chamber.

DETAILED DESCRIPTION OF THE INVENTION

Figure 1:
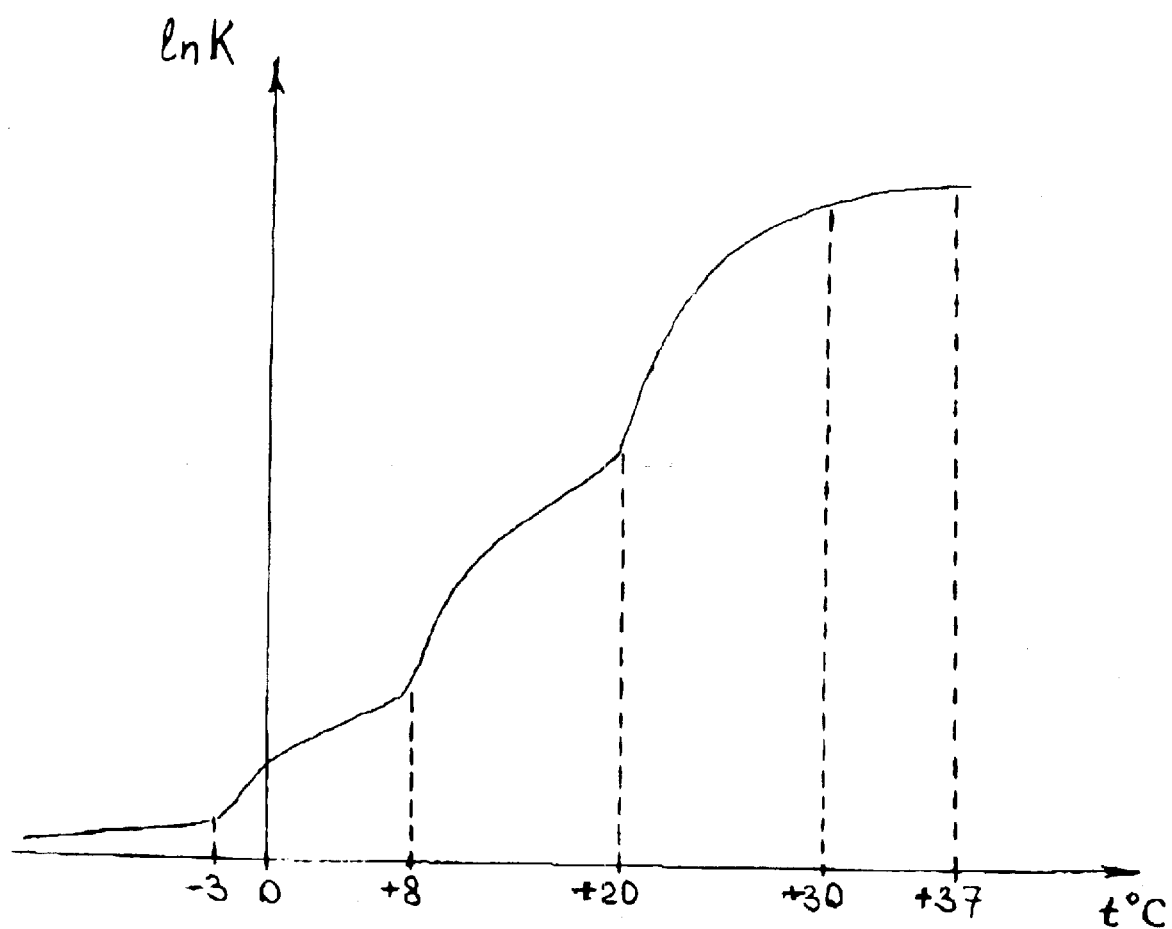
FIG. 1 shows a graph of In K versus temperature for rate of biochemical reaction.

The present invention provides compositions, methods and apparatuses for storing biological materials and, in particular, platelets, for an extended period of time. According to the present invention, functionally intact platelets can be recovered at high yields and used directly for platelet transfusions clinically.

1. Platelet Composition

The present invention provides various platelet compositions suitable for direct transfusion into a patient. According to one embodiment, a platelet composition comprises: a preservation medium comprising plasma and a gel-forming material in a concentration relative to the plasma such that the medium is in a sufficiently fluent state at a first temperature to allow platelets to move within the medium and is in a sufficiently gelatinous state at a second, lower temperature to substantially prevent platelets from moving freely within the medium; and platelets.

According to this embodiment, the first temperature is preferably about 37° C. and the second temperature is preferably about 5° C.

Platelets tend to activate upon contacting each other and aggregate. When a gel-forming material is added into a suspension of platelets in plasma, the resulted platelet preservation medium is in a sufficiently fluent state such that the platelets can move and distribute discretely within the medium following moderate agitations. When the platelet composition is cooled, the gel-forming material causes the preservation medium to become sufficiently gelatinous so as to form a physical barrier between the already distributed platelets. In this regard, platelets are prevented from moving freely within the gelatinous medium. The gelatinous medium also provides a structural support that maintains platelet morphology and minimizes deformation of the platelet membrane when the interior volume of the platelet changes during the cooling process. The gelatinous medium also lowers platelet metabolism by decreasing biochemical exchanges between the platelet and its environment. Inclusion of plasma in the preservation medium is believed to enhance platelet survival by simulating the platelet's native environment. Thus, retention of the functional integrity of platelets is improved under the storage conditions provided by the present invention. As a result, a higher percentage of the platelets can still perform their biological functions, such as promoting blood clotting, after being stored according to present invention.

The shelf-life of platelets may be successfully extended by storing the platelets in the preservation medium in a gelatinous state. The platelets may be stored within the preservation medium for at least 3 days, more preferably at least 5 days, and most preferably at least 7 days where at least 50% of the platelets are intact and functional after the storage period.

Also according to this embodiment, the platelets may be stored within the preservation medium for between 3 and 20 days, more preferably between 5 and 20 days. Longer storage of platelets is also possible.

Also according to this embodiment, the platelets may be stored within the preservation medium at a temperature less than 10° C. and preferably between −10° C. and 10° C. In one variation, the platelets are stored at a temperature between 0° C. and 10° C. at 1 ATM, more preferably at a temperature between 0° C. and 5° C. at 1 ATM. In another variation, the platelets are stored within the preservation medium at a temperature between −10° C. and 0° C. at a pressure greater than 10 ATM, more preferably at a temperature between −8° C. and −2° C. at a pressure greater than 10 ATM.

According to another embodiment, a platelet composition suitable for direct transfusion into a patient is provided comprising: a preservation medium comprising plasma and a gel-forming material in a concentration relative to the plasma such that the medium is in a sufficiently fluent state at a first temperature to allow platelets to move within the medium and is in a sufficiently gelatinous state at a second, lower temperature to substantially prevent platelets from moving freely within the medium; and platelets which have been stored within the preservation medium in a gelatinous state for at least 1 day at a pressure of at least 10 ATM and a temperature below 0° C. where at least 50% of the platelets are intact and functional after the at least 1 day.

According to this embodiment, the first temperature is preferably about 37° C. and the second temperature is preferably about 5° C.

According to this embodiment, the platelets may be stored within the preservation medium at a pressure of at least 30 ATM, more preferably at least 70 ATM, most preferably at least 200 ATM.

According to this embodiment, the platelets may be stored within the preservation medium for at least 3 days, more preferably at least 5 days, most preferably at least 7 days. Also according to this embodiment, the platelets may be stored within the preservation medium for between 3 and 20 days, more preferably between 5 and 20 days. Longer storage of platelets is also possible.

In regard to all of the compositions of the present invention, it preferred that at least 65% of the platelets are intact and functional after storage, more preferably at least 75% of the platelets, most preferably at least 85% of the platelets.

The gel-forming material preferably constitutes between 0.2% and 4% of the preservation medium although the concentration may vary depending on the particular gel-forming material used. Examples of gel-forming material that may be used include, but are not limited to, gelatin, agarose, agar, pectin, carob cassia and natural or synthetic water soluble gums. Many of the gel-forming materials are commercially available. They are typically extracted from natural sources and are often used as additive to various foods. Examples of water soluble polysaccharide gums include xanthan gum, konjac gum, guar gum, gum arabic, sodium alginate, carrageenan and irgacanth gum. Synthetic water soluble gel-forming material includes hydroxyethyl methacrylate.

The preservation medium may further include an energy source for increasing hypertonicity of the medium. The energy source preferably constitutes between 0 and 5% of the preservation medium, more preferably between 0.25 and 5% of the preservation medium, and most preferably between 0.5 and 5% of the preservation medium.

A wide variety of energy sources may be used. Most typically, the energy source is a carbohydrate, such as a sugar. Particular examples of energy sources include glucose, sucrose, mannose, fructose and galactose. Moreover, sucrose may repair damage in the cell membrane and glucose provides nutrients to sustain cell metabolism in the oxygen-poor conditions caused by the cooling process. Carbohydrates such as sucrose and glucose bind water, thus promoting gel formation and inhibiting osmotic pressure build-up within the platelets.

The preservation medium may further include water soluble salts. The salt preferably constitute between 0 and 2% of the preservation medium. Examples of salts include, but are not limited to, sodium chloride, potassium chloride, magnesium chloride, sodium phosphate, potassium phosphate and sodium gluconate. For example, sodium chloride prevents hemolysis by inhibiting the flow of water to the platelets during cooling. As the platelets are cooled below 20° C., the cytoplasm changes from a colloid to a gel, and free water leaves the cell. As the platelets are cooled even further, the hypertonic concentration of NaCl prevents water from reentering the platelets. Sodium chloride also lowers the freezing point of blood plasma by 2.5° C.

The preservation medium may further include an anticoagulant. Examples of anticoagulants that may be used include heparin, citrate dextrose, citrate phosphate dectrose, amantadine, ajoene and ticlopidine.

The preservation medium may further include amino acids. Examples of amino acids that may be used include arginine, lysine, aspartate and glutamate.

In a preferred embodiment, the preservation medium includes 1 to 3% gelatin. As it is cooled, the gelatin causes solidification of the preservation medium and the resulted gel matrix forms a physical barrier between platelets. Thus, the gel matrix formed suspends cells in the preservation medium and reduces sedimentation and clumping of platelets.

In a more preferred embodiment, the preservation solution includes 1.0 to 3.0% gelatin, 1.0 to 2.0% glucose, 1.0 to 3.0% sucrose, and 0.2 to 0.6% NaCl.

2. Methods for Platelet Storage

The present invention provides a variety of methods for storing platelets for direct transfusion into a patient. According to one embodiment, the method comprises the following steps:

1) forming a fluent platelet composition comprising platelets and a preservation medium including plasma and a gel-forming material in a concentration relative to the plasma such that the medium is in a sufficiently fluent state at a first temperature to allow platelets to move within the medium and is in a sufficiently gelatinous state at a second, lower temperature to substantially prevent platelets from moving freely within the medium;

2) cooling the fluent preservation medium to form a sufficiently gelatinous state to substantially prevent free movement of the platelets within the preservation medium; and 3) storing the platelets within the preservation medium in a gelatinous state for at least 3 days where at least 50% of the platelets are intact and functional after the at least 3 days.

According to this embodiment, the first temperature is preferably about 37° C. and the second temperature is preferably about 5° C., although different first and second temperatures may be employed.

For example, the platelet composition is formed by suspending platelets in the preservation medium that includes a gel-forming material and plasma at about 37° C. The preservation medium is in a fluent state so that the platelets can distribute discretely within the medium following moderate agitations. The platelet composition can be cooled gradually to about 5° C. where the gel-forming material causes the preservation medium to become sufficiently gelatinous so as to form a physical barrier between the already distributed platelets. Under such conditions, platelets are prevented from moving freely within the gelatinous medium and activating upon contacting each other. As a result, the platelets can be stored for a prolonged period of time and still maintain their functional integrity.

According to this embodiment, the platelets may be stored within the preservation medium for at least 3 days, more preferably at least 5 days and most preferably at least 7 days. Also according to this embodiment, the platelets may be stored within the preservation medium for between 3 and 20 days, more preferably between 5 and 20 days. Longer storage of platelets is also possible.

Also according to this embodiment, the platelets may be stored within the preservation medium at a temperature less than 10° C. and preferably between −10° C. and 10° C. In one variation, the platelets are stored at a temperature between 0° C. and 10° C. at 1 ATM, more preferably at a temperature between 0° C. and 5° C. at 1 ATM.

In another embodiment, a method is provided to store platelets at subzero temperatures and under pressure higher than atmospheric pressure. The method comprises the following steps:

1) forming a fluent platelet composition comprising platelets and a preservation medium including plasma and a gel-forming material in a concentration relative to the plasma such that the medium is in a sufficiently fluent state at a first temperature to allow platelets to move within the medium and is in a sufficiently gelatinous state at a second, lower temperature to substantially prevent platelets from moving freely within the medium;

2) cooling the fluent preservation medium to form a sufficiently gelatinous state to substantially prevent free movement of the platelets within the preservation medium; and 3) storing the platelets within the preservation medium in a gelatinous state for at least 1 day at a temperature below 0° C. and at a pressure of at least 10 ATM where at least 50% of the platelets are intact and functional after the at least 1 day.

According to this embodiment, the platelets are preferably stored within the preservation medium at a pressure of at least 30 ATM, more preferably at a pressure of at least 70 ATM, most preferably at a pressure of at least 200 ATM.

In another variation, the platelets are stored within the preservation medium at a temperature between −10° C. and 0° C. at a pressure greater than 10 ATM, more preferably at a temperature between −8° C. and −2° C. at a pressure greater than 10 ATM.

Also according to this embodiment, the platelets may be stored within the preservation medium for at least 3 days, more preferably at least 5 days, most preferably at least 7 days. Also according to this embodiment, the platelets may be stored within the preservation medium for between 3 and 20 days, more preferably between 5 and 20 days. Longer storage of platelets is also possible.

By using these methods, platelets are stored under conditions where their metabolism and biochemical reactions slow down and their functional integrity is preserved. The platelet composition stored at low temperature can be brought to a condition ready for transfusion into a patient by warming the composition up to about 37° C. where the gel-like composition melts to a sufficiently fluent state.

3. Physics of Subzero Pressurized Storage

Temperature is one of the most important parameters to be considered when storing living biological materials. When the temperature inside a cell drops too low, irreversible biochemical and structural changes occur. Several hundred biochemical reactions take place concurrently in the living cell. The rate of these biochemical reactions depends on several factors, including pressure, temperature, viscosity of the environment, pH, and concentrations of reactive molecules.

A metabolic process typically includes a series of intermediate processes, in which a substrate s is converted into a series of intermediate products $X_1, X_2, X_3 \ldots$ before being converted into a final product P. For each of these intermediate processes, the reactions may be catalyzed with different enzymes $E_0, E_1, E_2 \ldots$:

$$\begin{array}{ccc} E_0 & E_1 & E_2 \\ \end{array} \qquad \text{Equation (1)}$$
$$S \rightarrow X_1 \rightarrow X_2 \rightarrow X_3 \ldots \rightarrow P$$

Under normal conditions, the volume of substrate s transformed per unit of time equals the volume of product P obtained per unit of time:

$$-\frac{d[S]}{dt} = +\frac{d[P]}{dt} \qquad \text{Equation (2)}$$

where [s] and [P] are the concentrations of substrate s and product P. The concentration of the intermediate products $[X_1]$, $[X_2]$, $[X_3]$ under such conditions should also be constant:

$$\frac{d[X_1]}{dt} = \frac{d[X_2]}{dt} = \frac{d[X_3]}{dt} = 0 \qquad \text{Equation (3)}$$

Therefore, for each intermediate product, its rate of formation equals its rate of transformation. The concentrations of each intermediate product may be expressed in terms of the rates of formation and transformation:

$$\frac{d[X_3]}{dt} = -\frac{d[X_2]}{dt} = K_2 \cdot [X_2] \qquad \text{Equation (4)}$$

where $K_2$ is the constant of rate reaction constant of transformation of product $X_2$ and formation of product $X_3$. For steady state:

$$-\frac{d[S]}{dt} = +\frac{d[X_1]}{dt} = +\frac{d[X_2]}{dt} = +\frac{d[X_3]}{dt} \ldots = +\frac{d[P]}{dt} \qquad \text{Equation (5)}$$

From the above it follows that:

$$K_1 \cdot [X_1] = K_2 \cdot [X_2]$$

$$[X_1]:[X_2] = K_2:K_1 \qquad \text{Equation (6)}$$

Therefore, the concentration of each intermediate product is determined by its rate constants of formation and transformation.

Temperature dependence is defined by constant K of the rate of chemical reaction to Arrenius:

$$K = A \cdot e^{-E/RT} \qquad \text{Equation (7)}$$

where

A is the constant coefficient in some temperature interval;

E is the activating energy of chemical reaction per 1 mol of the substance;

R is the universal gas constant; and

T is the absolute temperature.

For most biochemical reactions, E>>RT. Taking the natural logarithm of both sides of Equation (7) gives:

$$\ln K = \ln A - \frac{E}{RT} \qquad \text{Equation (8)}$$

FIG. 1 shows a graph of ln K versus temperature. From 30° C. to 37° C., A is constant. For different chemical reactions E and A are different. As temperature decreases, there is a misbalance of reactions rates and Equation (5) no longer holds. This means the intermediate product concentrations corresponding to each of the biochemical reactions begin to change. This begins breakdown of cell structures, including the cell membrane, and can end in cell death.

Chemical reactions are either exothermic or endothermic, i.e. they either give off or absorb energy. Reactions taking place during hydrolysis can release large amounts of energy. The oxidation of 1 mol of glucose releases 2883 kJ of energy. Should the biochemical reaction rates slow down too much, irreversible process begin to take place finally leading to total destruction of the cell. Therefore, coefficient A becomes a function of temperature T.

As the temperature drops below 20° C., the lipid bi-layer of the cell membrane undergoes a phase transition from a colloid to a gel. The viscosity of a gel is much higher then that of its colloid. Consequently, rates of diffusion and active transportation of molecules through the cell membrane decrease sharply, resulting in a slowing down of the rate of biochemical reactions in a cell. As a result of the phase transformation of the cell membrane, the surface area of the lipid bi-lay surface and cell size reduce considerably due to the loss of water from the cell.

As the density of osmo-active substances increases, water molecules return to the cell thereby increasing osmotic pressure. Membrane tension reaches a critical point and may lose its barrier function. Membrane damage develops, resulting in morphological and structural changes, as well as loss of the ability for active adaptation.

As the temperature drops below 8° C., the cell cytoplasm undergoes a phase transformation into a gel. At this temperature, there is a sharp decrease in diffusion rate and active transportation of molecules, as well as in biochemical reaction rates.

As the temperature falls below −3° C., water crystallization begins to occur both inside and outside the cell. In the absence of cryoprotectors, water crystallization outside the cell leads to cell dehydration, decreased cell size, and increased concentrations of salt and other substances inside the cell. Water crystallization inside the cell results in structural cell membrane destruction.

Figure 2:
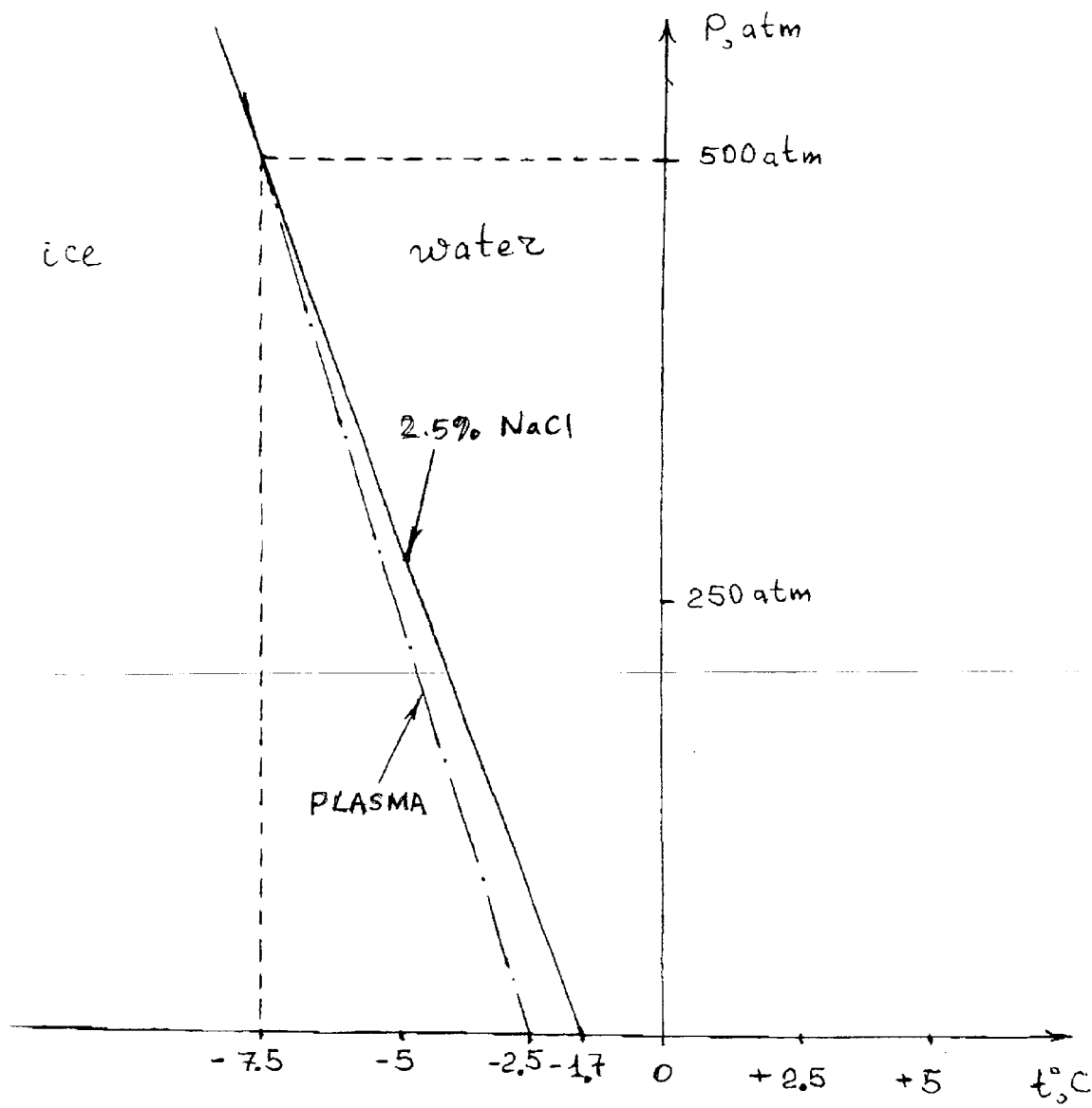
FIG. 2 the phase transition lines for plasma and a 2.5% NaCl solution.

FIG. 2 shows the phase transition lines for plasma and a 2.5% NaCl solution. At normal pressures, plasma freezes at −2.5° C. Plasma contains various chemical which lower the freezing point by interfering with the formation of the crystal lattice structure of ice. Cell structures can be cooled to −4° C. to −3° C. without water crystallization into cytoplasm. At normal pressures, the 2.5% NaCl solution freezes at −1.7° C.

Figure 3:
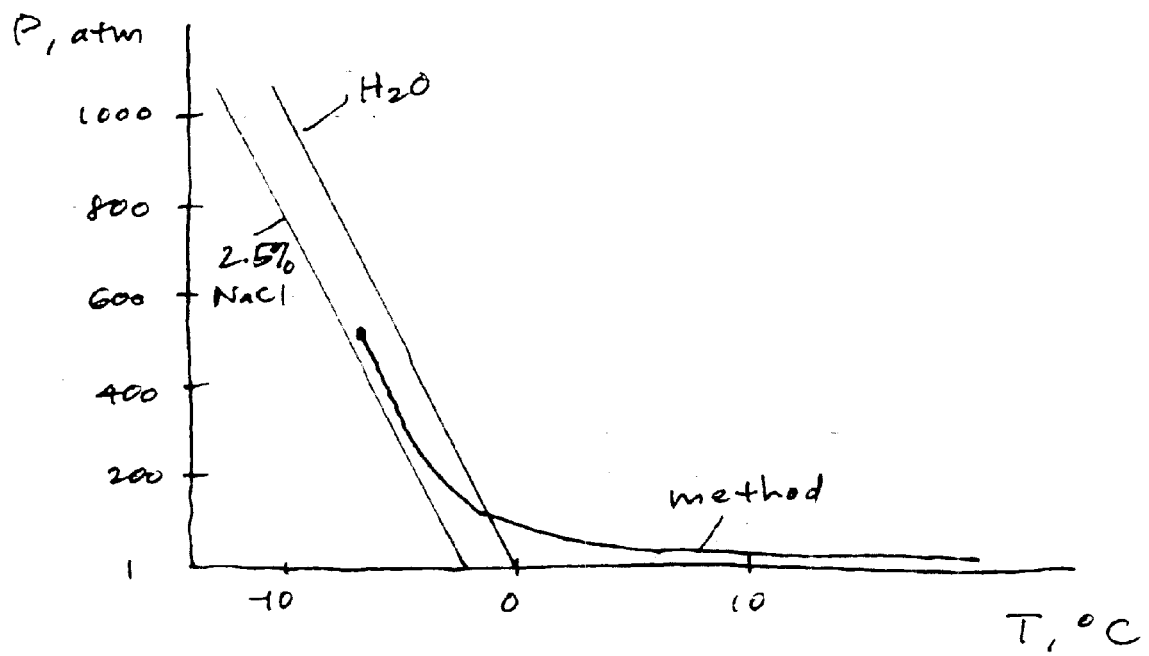
FIG. 3 shows another set of phase transition lines.

FIG. 3 shows the phase transition lines for water and a 2.5% NaCl solution. The addition of NaCl to water as lowers the freezing point, and thus allows lower temperatures to be achieved for a given pressure. The line shows one example of how a biological material may be subjected to a combination of high pressure and low temperature to prevent freezing.

4. Apparatus for Subzero Pressurized Storage

The present invention also provides apparatuses for the extended storage of biological materials, and, in particular, platelets. For example, the apparatuses can be used to store platelets suspended in a preservation medium comprising plasma and a gel-forming material in a concentration relative to the plasma such that the medium is in a sufficiently fluent state at about 37° C. to allow platelets to move within the medium and is in a sufficiently gelatinous state at about 5° C. to substantially prevent platelets from moving freely within the medium.

Figure 4:
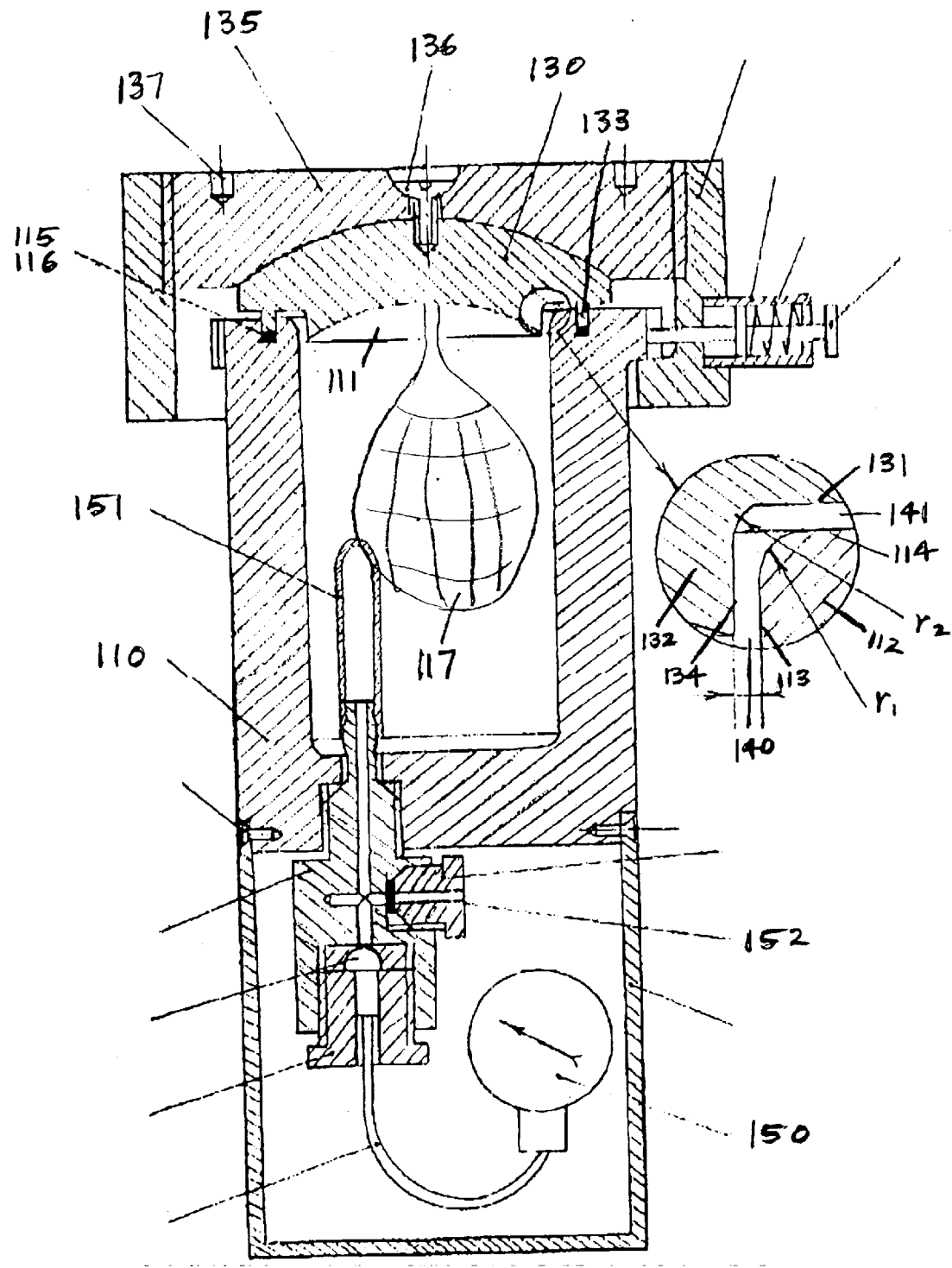
FIG. 4 shows a cross-sectional view of a biological material preservation apparatus of the present invention.

FIG. 4 shows an assembled view of one embodiment of a biological material preservation apparatus 100 of the present invention. Preservation apparatus 100 includes a chamber 110 and a cover 130.

Figure 5A:
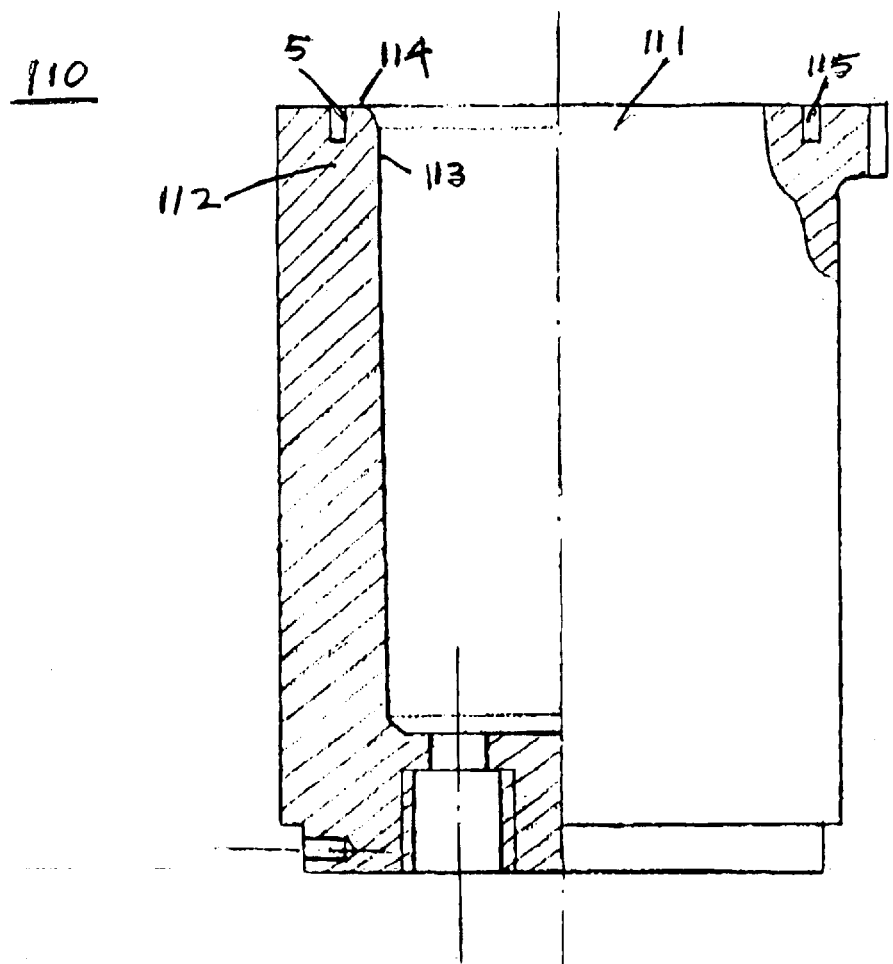
FIGS. 5A–5B shows a side cutaway and top views, respectively, of the chamber of the preservation apparatus.
Figure 5B:
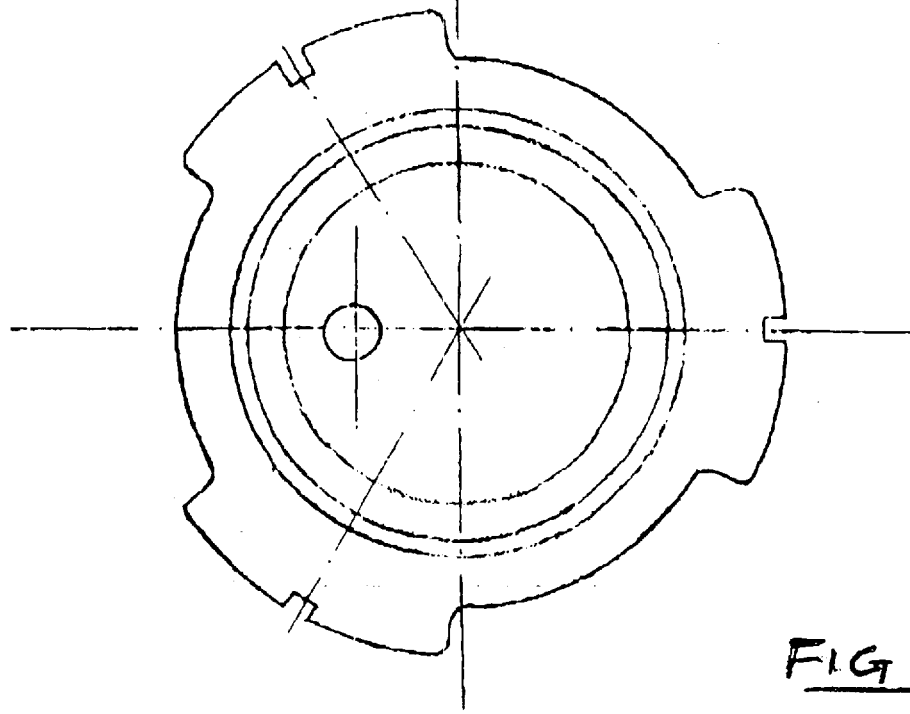

FIGS. 5A–5B show side cutaway and top views, respectively, of chamber 110. Chamber 110 includes a mouth 111 and a lip 112. Lip 112 includes an inside surface 113 and a top surface 114. Inside surface 113 and top surface 114 meet at a first radius $r_1$. Top surface 114 includes a channel 115. Channel 115 may have a sealing device 116 seated at a bottom of channel 115, such as an O-ring or rubber gasket. Chamber 110 may be manufactured in different sizes to accommodate a platelet bag, blood donation bag, heart, liver, kidney, or other bags and biological materials.

Figure 6:
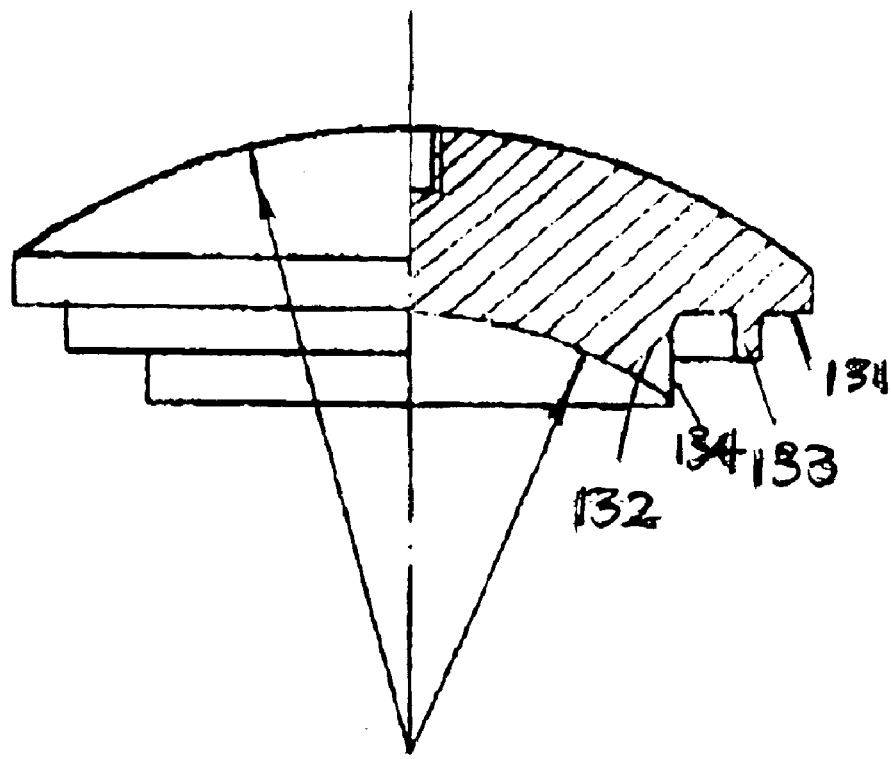
FIG. 6 shows a side view of the cover of the preservation apparatus.

FIG. 6 shows a cutaway view of cover 130. Cover 130 is configured to mate with and seal chamber 110. Cover 130 includes a bottom surface 131. Bottom surface 131 includes a protrusion 132 and a sealing structure 133. Bottom surface 131 and protrusion 132 meet at a second radius $r_2$. Protrusion 132 is inserted into mouth 111 of chamber 110 when cover 130 is mated with chamber 110. Protrusion 132 includes a side surface 134. Side surface 134 of protrusion 132 and inside surface 113 of lip 112 define a first gap 140 and are substantially parallel when cover 130 is mated with chamber 110. Bottom surface 132 of cover 130 and top surface 118 of lip 114 define a second gap 141 and are substantially parallel when cover 130 is mated with chamber 110. Second gap 141 has a length greater than a width of first gap 140. Sealing structure 133 is inserted into channel 115 of lip 112 when cover 130 is mated with chamber 110.

Figure 7A:
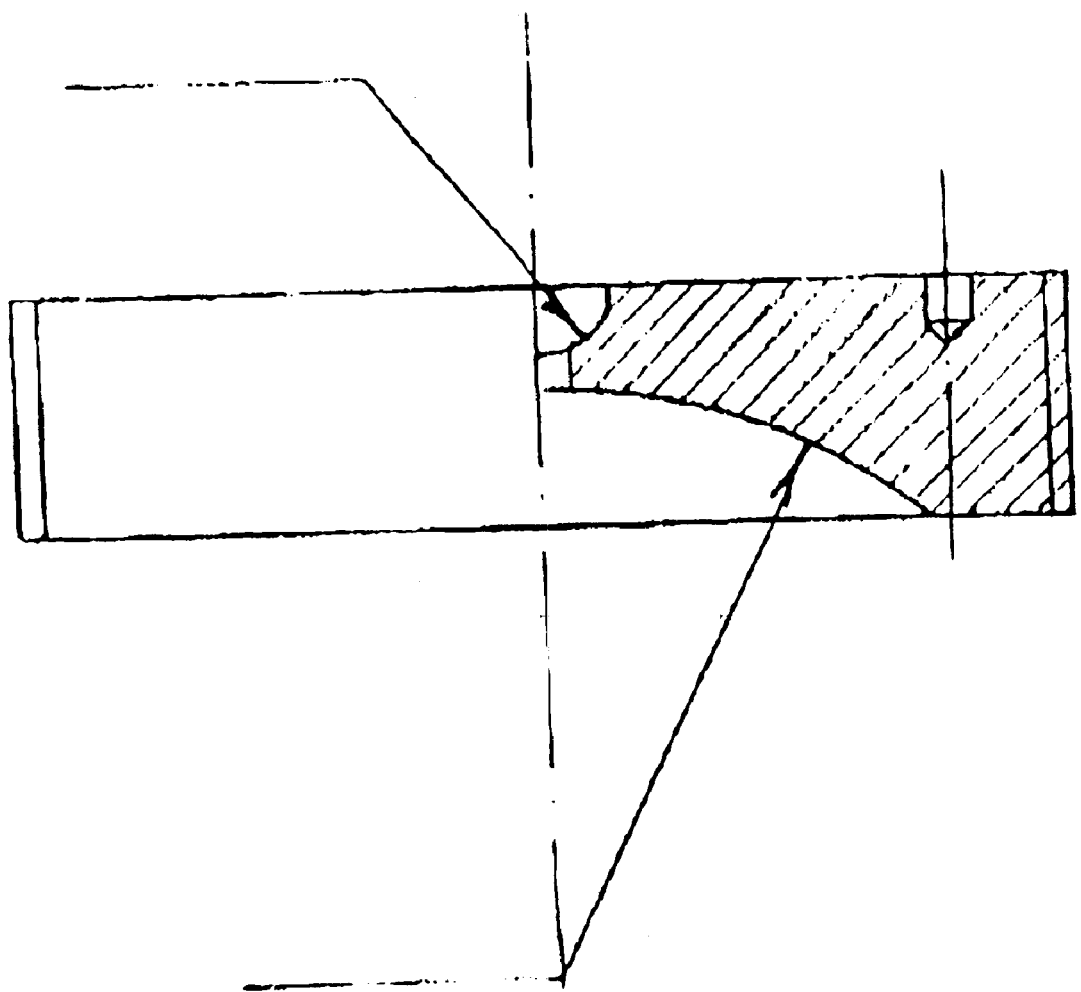
FIGS. 7A–7C show a cover retaining device of the preservation apparatus.
Figure 7B:
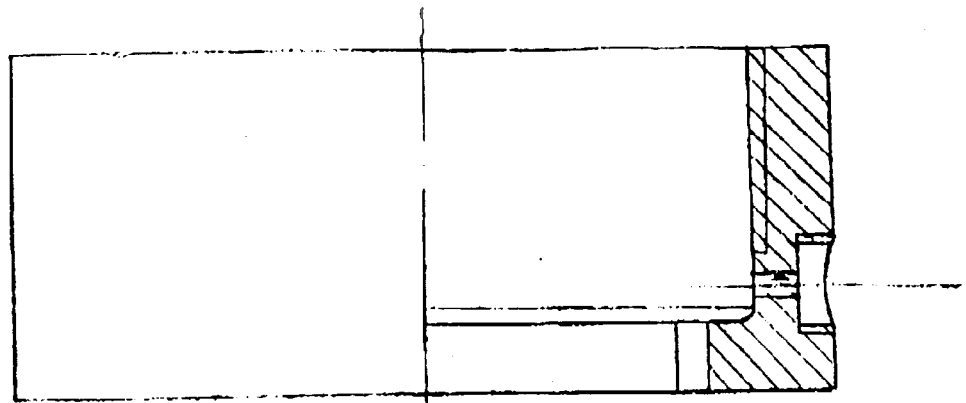
Figure 7C:
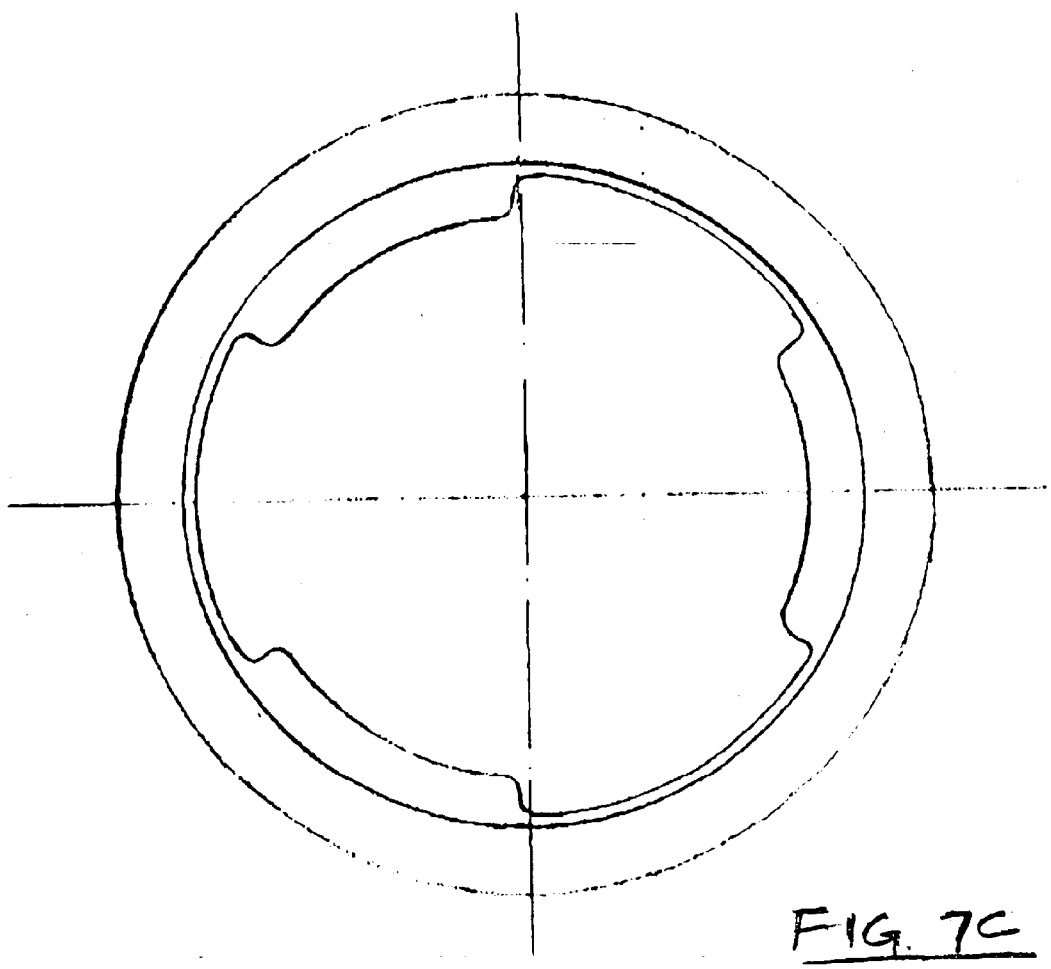

Cover 130 may be made to be a spherical section, which allows cover 130 to be made lighter and with less material than a flat cover 130 without sacrificing strength. When preservation apparatus 100 is filled with, for example, saline solution and then cooled below the freezing point, ice will begin to form along the walls of chamber 110 and cover 130. Ice will form in first gap 140 and second gap 141 and help to seal chamber 110. Thus, the high pressures within chamber 110 are largely borne by this ice seal, thus minimizing the need to make channel 115, sealing device 116, and sealing structure 133 extremely robust and capable of withstanding such high pressures. Channel 115, sealing device 116, and sealing structure 133 only need to withstand pressures of up to 10 atm before the ice seal takes over. The sizes of first gap 140 and second 141 are not critical, but may be minimized so that ice fills them before the seal is subjected to pressures above 10 atm. In one embodiment, first gap 140 and second gap 141 may be less than 2.0 mm in width. Chamber 110 includes a suspension device 117 which prevents biological material or bag placed within pressure chamber from coming into contact with the walls of chamber 110. Suspension device 117 may be a net, a platform, a spacer, or any other suitable device. Cover 130 may be designed to be sealed to chamber 110 directly, or with the aid of a cover retaining device 135. Cover retaining device 135 may be designed to allow cover 130 to be installed and removed quickly and easily. Cover retaining device 135 may be coupled to chamber 110 via a bayonet-style connection, threads, or any other suitable coupling method. Cover retaining device 135 may include a centering pin 136 to keep cover retaining device 135 centered or attached to cover 130. Cover retaining device 135 may also include holes 137 to allow a wrench or other tool to be used with cover retaining device 135. Cover retaining device 135 may be produced in two separated pieces to simplify manufacturing. FIGS. 7A–7C show cutaway and top views of a two-piece cover retaining device 135.

Preservation apparatus 100 may include a pressure gauge 150 with an elastic membrane 151 placed within chamber 110. Pressure gauge 150 may include a relief valve 152 which prevents pressure within preservation apparatus 100 from exceeding a predetermined maximum.

By utilizing the features of the present invention, the following objectives for preserving biological materials, in particular, platelets, are achieved:

1. Mechanically suspending the biological materials in a preservation medium.
2. Storing the biological materials at the lowest possible temperature while maintaining them in a liquid state. Under these conditions, the rate of biochemical reactions are relatively slow and therefore, the rates of change in the concentrations of intermediate products is small.
3. Slowly cooling solutions with platelets to allow free and safe water flow from the cell to prevent membrane tension from reaching a bursting point during the phase transmission from a colloid to a gel. On the other hand, the cooling rate should be high enough to prevent intermediate biochemical reactions from causing irreversible changes in cell structure.

EXAMPLES

1. Method of Platelet Preservation

The following is one example of the method of the present invention for preserving blood platelets. Heparin may be used as an anticoagulant before this process is begun.

(1) Mix the platelets with a preservation solution of 2.9% gelatin, 0.44% sucrose, 1.17% glucose, and 0.49% NaCl.

(2) Seal the platelets and preservation solution into a storage bag, making sure that any air has been pumped out The storage bag may be any standard platelet storage bag such as a flexible silicone rubber bag.

(3) Cool the platelets and preservation solution to 15° C. within 1 hour. Continuous agitation is required until the preservation solution becomes a gel.

(4) Cool the storage bag to 6° C. to 8° C. within 1 to 1.5 hours.

(5) Cool the preservation apparatus to 6° C. to 8° C.

(6) Insert the storage bag into the preservation apparatus using the suspension device.

(7) Fill the preservation apparatus with a pressure transfer fluid of 2.5% NaCl solution.

(8) Seal the preservation apparatus, making sure it is completely full and no air is trapped inside.

(9) Cool the preservation apparatus to $-7.5 \pm 0.2°$ C. within 1.5 to 2 hours. The pressure transfer fluid is a fluid which expands when cooled or frozen, and thus will be able to exert a pressure upon the bag within the substantially fixed volume of the preservation apparatus. With the 2.5% NaCl solution, the water will begin to freeze at the walls of the pressure chamber. As the ice is formed at the walls of the pressure chamber, the expansion will create the high pressures required within the preservation apparatus, which will be transferred by the unfrozen fluid immediately surrounding the storage bag to the storage bag. The NaCl lowers the freezing point of the pressure transfer fluid, thus allowing the low temperatures required to be achieved before the entire volume of the pressure transfer fluid becomes frozen. The preservation solution has a lower freezing point than the pressure transfer fluid. The pressure inside the preservation apparatus will rise to 500 atm. As ice begins to form, pressure within the preservation apparatus will increase because ice and water are essentially non-compressible. The relationship between temperature and pressure here is consistent and predictable. The combination of the preservation solution, the high storage pressure, and the low storage temperature allows the platelets to be stored for up to 15 days. Erythrocytes may be stored up to 30 days and leukocytes up to 22 days using this method.

(10) When the platelets are needed for use, allow the preservation apparatus to thaw completely at room temperature, approximately 20° C., before opening the preservation apparatus. Because the components in the preservation solution are all nontoxic, the platelets may be used immediately without further preparation.

2. Studies of Platelet Survival

Human blood platelets suspended in plasma and contained in standard platelet bags were mixed with a concentrated gelatin stock solution at 37° C. The concentrated gelatin stock solution also contained sugar and sodium chloride. Typically, the amount of gelatin solution added was ¼ the volume of plasma. For example, 25 ml of a gelatin stock solution containing 3.5% gelatin and 10% glucose was added to 100 ml of plasma with platelets, resulting in a final solution at 0.7% gelatin and 2% glucose. The final concentration of platelets in the platelet bag is about 300,000 per $\mu$l.

The platelet compositions were stored at a refrigerator temperature or in an preservation apparatus according to the present invention at subzero temperatures. Following certain periods of time (n days) storage, the platelet compositions were warmed to about 37° C. and analyzed for post-storage ($D_n$) activity, such as platelet aggregation, as compared to the activity of platelets before storage ($D_0$) by using standard methods performed by hospital clinical laboratories.

Typically, platelet aggregation is performed by adding a stimulus, such as 10 $\mu$M adenosine diphosphate (ADP) and 14 $\mu$g ristocetin, to a suspension of platelets in a curvette or on a slide. Methods and amounts of stimuli typically used are well known to those skilled in the art. The stimulating agent binds to receptors on the platelets and causes the platelets to release substances from granules and initiates a cascade of events resulting in platelets binding to each other and falling out of the suspension. Typically, the aggregation of platelets is indicated by an increased ability of the solution to allow passage of light (increased % transmission or decreased turbidity). The time platelets respond to each stimulus was recorded in seconds. The survival rate of platelets was measured by counting post-storage platelets with intact morphology under a microscope and comparing with the platelets before the storage.

Table I lists the constituents of the preservation medium, the survival rates of the platelets and aggregation response times of the platelets when exposed to ristocetin or ADP and after the platelets have been stored in preservation media for a listed period of time (n days) at a refrigerator temperature 4° C.

TABLE I

| | | | | | | Aggregation Response (sec.) | |
| --- | --- | --- | --- | --- | --- | --- | --- |
| Gelatin | Sucrose | Glucose | NaCl | n days at 4° C. | Survival | Ristocetin ($D_o/D_n$) | ADP ($D_o/D_n$) |
| 0.45% | 2.0% | 2.0% | 0.5% | 5 d | 82% | 9/7 | 9/8 |
| 0.7% | 2.0% | 2.0% | 0.5% | 5 d | 100% | 14/7 | 11/7 |
| 1.5% | 2.0% | 2.0% | 0.5% | 5 d | 88% | 14/12 | 17/12 |

Table II lists the constituents of the preservation medium, the survival rates of the platelets and aggregation response times of the platelets when exposed to ristocetin and adenosine diphosphate (ADP) after the platelets have been stored in preservation media for a listed period of time at a sub-zero temperature (−4 to −10° C.).

TABLE II

| | | | | | | Aggregation Response (sec.) | |
| --- | --- | --- | --- | --- | --- | --- | --- |
| Gelatin | Sucrose | Glucose | NaCl | n days at <0° C. | Survival | Ristocetin ($D_o/D_n$) | ADP ($D_o/D_n$) |
| Plasma | | | | 5d | 6% | 11/23 | 11/43 |
| 1.5% | 0.5% | 1.0% | 0.5% | 5d | 100% | 11/8 | 12/10 |
| 3.0% | 0.5% | 1.0% | 0.5% | 5d | 100% | 11/6 | 12/7 |
| 0.5% | 0.5% | 1.0% | 0.5% | 5d | 76% | 9/9 | 9/10 |
| 1.5% | 2.0% | 1.0% | 0.5% | 5d | 100% | 11/8 | 10/9 |
| 1.5% | 1.5% | 1.0% | 0.5% | 5d | 100% | 9/14 | 10/17 |
| 0.7% | 2.0% | 2.0% | 0.5% | 11d | 45% | 9/10 | 10/13 |
| 1.5% | 2.0% | 2.0% | 0.5% | 11d | >50% | 9/8 | 11/8 |
| 0.7% | 2.0% | 2.0% | 0.5% | 13d | 86% | 9/4 | 10/7 |
| 1.5% | 2.0% | 2.0% | 0.5% | 13d | 100% | 11/6 | 14/5 |

As can be seen from the results shown in Table I and II, platelets were stored for five or more days with high survival rates.

The foregoing description of the invention has been presented for purposes of illustration and description. It is not intended to be exhaustive or to limit the invention to the precise forms disclosed. Many modifications and variations will be apparent. It is intended that the scope of the invention be defined by the following claims and their equivalents.

What is claimed is:

1. A method for storing platelets in a nonfrozen state for direct transfusion into a patient comprising:
    forming a fluent platelet composition comprising platelets and a preservation medium including plasma and a gel-forming material in a concentration relative to the plasma such that the medium is in a sufficiently fluent state at about 37° C. to allow platelets to move within the medium and is in a sufficiently gelatinous state at about 5° C. to substantially prevent platelets from moving freely within the medium;
    cooling the fluent preservation medium to form a sufficiently gelatinous state to substantially prevent free movement of the platelets within the preservation medium; and
    storing the platelets within the preservation medium in a gelatinous state for at least 3 days at a pressure of at least 10 ATM and a temperature below 0° C. where at least 50% of the platelets are intact and functional based on adenosine diphosphate induced platelet aggregation assay after at least 3 days.

2. The method for storing platelets according to claim 1, wherein the platelets are stored within the preservation medium for at least 5 days where at least 50% of the platelets are intact and functional after at least 5 days.

3. The method for storing platelets according to claim 1, wherein the platelets are stored within the preservation medium for at least 7 days where at least 50% of the platelets are intact and functional after at least 7 days.

4. The method for storing platelets according to claim 1, wherein the platelets are stored within the preservation medium for between 3 and 20 days where at least 50% of the platelets are intact and functional after at least 3 and 20 days.

5. The method for storing platelets according to claim 1, where the platelets are stored for at least 3 days within the preservation medium at a temperature between −10° C. and 0° C. at a pressure greater than 10 ATM.

6. The method for storing platelets according to claim 1, where the platelets are stored for at least 3 days within the preservation medium at a temperature between −8° C. and −2° C. at a pressure greater than 10 ATM.

7. A method for storing platelets for direct transfusion into a patient comprising:
    forming a fluent platelet composition comprising platelets and a preservation medium including plasma and a gel-forming material in a concentration relative to the plasma such that the medium is in a sufficiently fluent state at a first temperature to allow platelets to move within the medium and is in a sufficiently gelatinous state at a second, lower temperature to substantially prevent platelets from moving freely within the medium;
    cooling the fluent preservation medium to form a sufficiently gelatinous state to substantially prevent free movement of the platelets within the preservation medium; and
    storing the platelets within the preservation medium in a gelatinous state for at least 1 day at a temperature below 0° C. and at a pressure of at least 10 ATM where at least 50% of the platelets are intact and functional after at least 1 day.

8. The method according to claim 7, wherein the first temperature is about 37° C. and the second temperature is about 5° C.

9. The method for storing platelets according to claim 7, wherein the platelets are stored within the preservation medium at a pressure of at least 70 ATM.

10. The method for storing platelets according to claim 7, wherein the platelets are stored within the preservation medium at a pressure of at least 200 ATM.

11. The method for storing platelets according to claim 7, wherein the platelets are stored within the preservation medium for at least 3 days where at least 50% of the platelets are intact and functional after at least 3 days.

12. The method for storing platelets according to claim 7, wherein the platelets are stored within the preservation medium for at least 5 days where at least 50% of the platelets are intact and functional after at least 5 days.

13. The method for storing platelets according to claim 7, wherein the platelets are stored within the preservation medium for at least 7 days where at least 50% of the platelets are intact and functional after at least 7 days.

14. The method for storing platelets according to claim 7, wherein the platelets are stored within the preservation medium for between 3 and 20 days where at least 50% of the platelets are intact and functional after at least 3 and 20 days.

15. The method for storing platelets according to claim 7, wherein at least 65% of the platelets are intact and functional after at least 3 days.

16. The method for storing platelets according to claim 7, wherein at least 75% of the platelets are intact and functional after at least 3 days.

17. The method for storing platelets according to claim 7, wherein at least 85% of the platelets are intact and functional after at least 3 days.

* * * * *